United States Patent
Wang et al.

(10) Patent No.: US 10,408,752 B2
(45) Date of Patent: Sep. 10, 2019

(54) PLASMONIC SENSOR (71) Applicant: National Taiwan University, Taipei (TW)

(72) Inventors: Cheng Wang, Taipei (TW); Li-Wei Nien, Taipei (TW); Chun-Hway Hsueh, Taipei (TW); Hsin-Chia Ho, Taipei (TW); Yi-Chen Lai, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 15/716,518

(22) Filed: Sep. 27, 2017

(65) Prior Publication Data
US 2018/0106721 A1    Apr. 19, 2018

Related U.S. Application Data (60) Provisional application No. 62/409,839, filed on Oct. 18, 2016.

(51) Int. Cl.
*G01N 21/43*    (2006.01)
*G01N 21/25*    (2006.01)
(Continued)

(52) U.S. Cl.
CPC ............ *G01N 21/43* (2013.01); *G01N 21/25* (2013.01); *G01N 21/554* (2013.01);
(Continued)

(58) Field of Classification Search
CPC ...... G01N 21/55; G01N 21/658; G01N 29/34; G01N 29/2418; G01N 33/54373;
(Continued)

(56) References Cited

U.S. PATENT DOCUMENTS 5,629,213 A * 5/1997 Kornguth ............... B82Y 30/00
                                                      356/445
6,278,540 B1 * 8/2001 Wang ..................... G02F 1/315
                                                      359/245
(Continued)

FOREIGN PATENT DOCUMENTS

CN    103805920         5/2014
JP    2002131319 A  *  5/2002
TW    I237346            8/2005

OTHER PUBLICATIONS

Cheng Wang et al., "Viscous flow and viscosity measurement of low-temperature imprintable AuCuSi thin film metallic glasses investigated by nanoindentation creep," Materials & Design, vol. 123, Jun. 5, 2017, pp. 112-119.

(Continued)

*Primary Examiner* — Sang H Nguyen
(74) *Attorney, Agent, or Firm* — JCIPRNET (57) ABSTRACT

A plasmonic sensor includes at least a substrate and a thin film metallic glass formed on the substrate. The dielectric constant ($\varepsilon_r$) of the thin film metallic glass is negative. Since the thin film metallic glass with negative $\varepsilon_r$ is used in the plasmonic sensor, the material cost can be significantly reduced, the mechanical property can be improved, and the optoelectronic property can be increased. Since the thin film metallic glass is a kind of supercooled alloy with amorphous structure, it can be applied for imprinting deformation and amorphous without grain boundary scattering.

9 Claims, 7 Drawing Sheets

(51) Int. Cl.
*G01N 21/552* (2014.01)
*G01N 21/65* (2006.01)

(52) U.S. Cl.
CPC ..... *G01N 21/658* (2013.01); *G01N 2021/258* (2013.01); *G01N 2021/434* (2013.01)

(58) Field of Classification Search
CPC ............. G01N 21/43; G01N 2021/434; G01N 2021/258; G02B 5/0816; H01L 21/3088; H01L 21/31144; H01L 21/3086
See application file for complete search history.

(56) References Cited

U.S. PATENT DOCUMENTS

| | | | | |
|---|---|---|---|---|
| 7,394,962 | B2* | 7/2008 | Lee | G02B 6/1226 385/129 |
| 7,939,345 | B2* | 5/2011 | Wark | B82Y 30/00 436/164 |
| 8,431,208 | B2 | 4/2013 | Demetriou et al. | |
| 8,641,839 | B2 | 2/2014 | Schroers et al. | |
| 9,604,269 | B2 | 3/2017 | Kumar et al. | |
| 2004/0141300 | A1* | 7/2004 | Takubo | G01N 21/6428 362/5 |
| 2006/0045809 | A1* | 3/2006 | Shirai | G01N 21/554 422/82.11 |
| 2007/0211254 | A1* | 9/2007 | Matsushita | G01N 21/553 356/445 |
| 2008/0099175 | A1 | 5/2008 | Chu et al. | |
| 2008/0248222 | A1* | 10/2008 | Ohara | B32B 15/01 428/34.6 |
| 2009/0116020 | A1* | 5/2009 | Wu | G01N 33/54373 356/445 |
| 2009/0121272 | A1* | 5/2009 | Kim | B22F 1/0018 257/315 |
| 2011/0037981 | A1 | 2/2011 | Zhu et al. | |
| 2012/0327417 | A1* | 12/2012 | Amako | G01N 21/658 356/445 |
| 2013/0003066 | A1* | 1/2013 | Han | G02F 1/0072 356/432 |
| 2013/0193544 | A1* | 8/2013 | Ozcan | B82Y 15/00 257/432 |
| 2013/0213477 | A1* | 8/2013 | Nakayama | H01L 51/447 136/263 |
| 2013/0224886 | A1* | 8/2013 | Iwasaki | G01F 1/704 436/525 |
| 2014/0004507 | A1* | 1/2014 | Malic | B82Y 30/00 435/6.1 |
| 2014/0140054 | A1* | 5/2014 | Hashimura | C23C 14/046 362/231 |
| 2014/0226139 | A1* | 8/2014 | Csete | G02B 5/1809 355/53 |
| 2014/0231965 | A1* | 8/2014 | Washiya | H01L 21/3088 257/618 |
| 2014/0242573 | A1* | 8/2014 | Sugimoto | G01N 21/658 435/5 |
| 2015/0053312 | A1* | 2/2015 | Chu | C22C 45/10 148/403 |

OTHER PUBLICATIONS

Cheng Wang et al., "Au-based thin film metallic glasses for plasmonic sensor applications," SPIE Optics +Optoelectronics, Conference 10231, Session 3, Apr. 24, 2017, pp. 1-3.

* cited by examiner

PLASMONIC SENSOR

CROSS-REFERENCE TO RELATED APPLICATION

This application claims the priority benefit of U.S. provisional application Ser. No. 62/409,839, filed on Oct. 18, 2016. The entirety of the above-mentioned patent application is hereby incorporated by reference herein and made a part of this specification.

BACKGROUND OF THE INVENTION

Field of the Invention

The invention relates to a plasmonic sensing technique, and more particularly, to a plasmonic sensor having a thin film metallic glass (TFMG).

Description of Related Art

Surface plasmon is a concept related to coherent oscillation of conduction electrons on a metal surface excited by electromagnetic radiation at a metal-dielectric interface. Since surface plasmon is sensitive to the change of refractive index around metallic structures, it has attracted much attention and shown great potential in the field of optical sensing.

In general, two types of surface plasmon modes have been used in plasmon-based sensing, which are propagating surface plasmon resonances (PSPRs) and localized surface plasmon resonances (LSPRs). PSPRs are the resonances induced by the evanescent electromagnetic waves bound by planar metal-dielectric interfaces, and LSPRs are the resonances resulting from the electromagnetic waves confined on the surface of metallic nanostructures (e.g., periodic nanoarrays or individual nanoparticles). When the target analyte is bound onto the metal surface resulting in the local refractive index change, PSPR and LSPR sensors can sense it and transduce the binding event without labels (e.g., chromophore and fluorophore), which are required for conventional optical sensors.

In most of PSPR sensors, a precious metal such as Au, Ag or Pt is utilized as sensing element, and thus the cost is extremely high. On the other hands, for forming nanostructures, imprinting process is preferred for the fabrication of LSPR sensors. However, most polymers used for imprinting have poor mechanical strength at room temperature.

SUMMARY OF THE INVENTION

The invention provides a plasmonic sensor for significantly reducing the material cost, improving mechanical property, and increasing optoelectronic property.

A plasmonic sensor of the invention includes at least a substrate and a thin film metallic glass formed on the substrate. The dielectric constant ($\varepsilon_r$) of the thin film metallic glass is negative.

In an embodiment of the invention, the thin film metallic glass is selected from the group consisting of: Au-based metallic glass, Cu-based metallic glass, Ag-based metallic glass, or Pt-based metallic glass.

In an embodiment of the invention, the Au-based metallic glass includes 30-80 at. % Au, 10-60 at. % Cu, and 5-40 at. % Si.

In an embodiment of the invention, a thickness of the thin film metallic glass is 10 nm to 10,000 nm.

In an embodiment of the invention, the substrate comprises glass substrate, silicon substrate, sapphire substrate, metal substrate, or flexible substrate.

In an embodiment of the invention, the thin film metallic glass is an imprinted film consisting of a plurality of patterns, and the patterns are arranged periodically or randomly.

In an embodiment of the invention, each of the patterns is extruded from the bottom surface of the imprinted film.

In an embodiment of the invention, each of the patterns is intruded into the top surface of the imprinted film.

In an embodiment of the invention, each of the patterns has a nano-scale size or a micro-scale size.

In an embodiment of the invention, the plasmonic sensor may be applied to be a propagating surface plasmon resonance (PSPR) sensor or a localized surface plasmon resonances (LSPR) sensor.

Based on the above, the plasmonic sensor according to the invention has a thin film metallic glass, and thus it may significantly reduce the material cost, improve mechanical property, and is suitable for mass production. Moreover, since the thin film metallic glass has a negative dielectric constant ($\varepsilon_r$), the optoelectronic property related to surface plasmon resonances may be improved.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Embodiments are provided hereinafter and described in detail with reference to figures. However, the embodiments provided are not intended to limit the scope of the invention. Moreover, the figures are only descriptive and are not drawn to scale. For ease of explanation, the same devices below are provided with the same reference numerals.

Moreover, terms such as "first" and "second" used herein do not represent order, and it should be understood that they are only for differentiating devices or operations having the same technical terms.

Moreover, terms such as "contain", "include" and "have" used in the present specification are all open terms, i.e., contains but not limited to.

Figure 1:
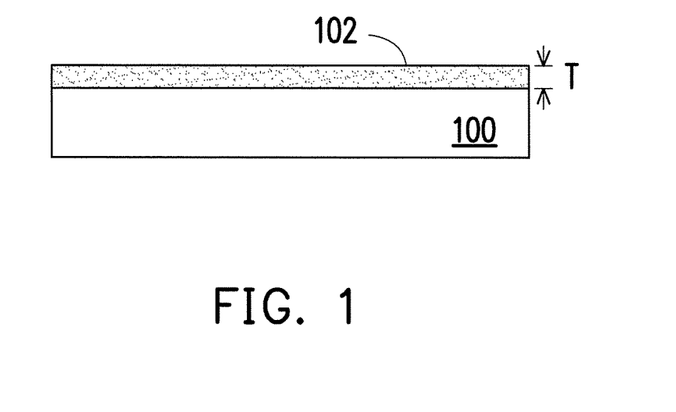
FIG. 1 is a cross-sectional schematic diagram of a plasmonic sensor according to an embodiment of the invention.

FIG. 1 is a cross-sectional schematic diagram of a plasmonic sensor according to an embodiment of the invention.

Referring to FIG. 1, a plasmonic sensor includes at least a substrate 100 and a thin film metallic glass 102 formed on the substrate 100. The dielectric constant ($\varepsilon_r$) of the thin film metallic glass 102 is negative. In the embodiment, the thin film metallic glass 102 is selected from the group consisting of: Au-based metallic glass, Cu-based metallic glass, Ag-based metallic glass, or Pt-based metallic glass, for instance. Accordingly, the plasmonic sensor of FIG. 1 may be applied to be a propagating surface plasmon resonance (PSPR) sensor. In one embodiment, the Au-based metallic glass, for instance, includes 3-80 atomic percent (at. %) Au, 10-60 at. % Cu, and 5-40 at. % Si.

In FIG. 1, the thin film metallic glass 102 has, for example, a thickness of 10 nm to 10,000 nm, but it is not limited thereto. In other embodiments, the thickness of the thin film metallic glass 102 may be more than 10 nm so as to apply for different plasmonic sensors. The substrate 100 includes, for example, glass substrate, silicon substrate, sapphire substrate, metal substrate, or flexible substrate. Since the thin film metallic glass 102 has a glass transition temperature ($T_g$) less than certain degree, the substrate 100 can be the flexible substrate made of thermoplastic or thermoset material. For example, the Au-based metallic glass has about 60° C. of $T_g$, and others may have about 300° C. of $T_g$.

Figure 2:
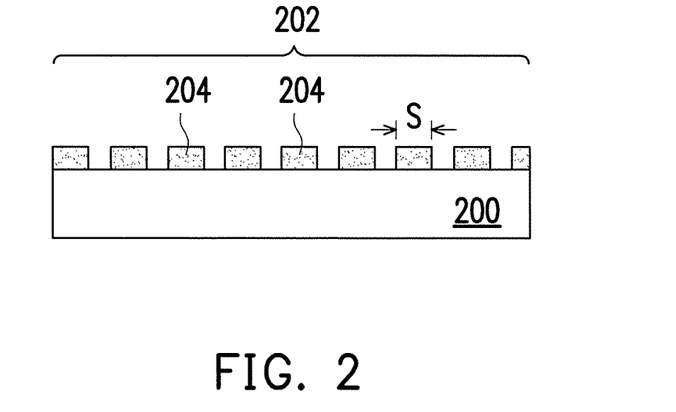
FIG. 2 is a cross-sectional schematic diagram of a plasmonic sensor according to another embodiment of the invention.

FIG. 2 is a cross-sectional schematic diagram of a plasmonic sensor according to another embodiment of the invention.

Referring to FIG. 2, a plasmonic sensor includes at least a substrate 200 and a thin film metallic glass 202 formed on the substrate 200. The dielectric constant ($\varepsilon_r$) of the thin film metallic glass 202 is negative, and a material or a thickness thereof can refer to that in above embodiment. Moreover, the thin film metallic glass 202 is an imprinted film consisting of a plurality of patterns 204 arranged periodically, and thus the plasmonic sensor of FIG. 2 may be applied to be a localized surface plasmon resonances (LSPR) sensor. However, the invention is not limited thereto. In other embodiment, the patterns 204 may be arranged randomly. Each of the patterns 204 is extruded from a bottom surface of the thin film metallic glass 202, wherein the bottom surface is in direct contact with the substrate 200. For the LSPR sensor, the resonance excited by the electromagnetic wave interacting with the subwavelength structures is the key factor for detecting the change in the refractive index of the surrounding medium. Therefore, the thin film metallic glass 202, a kind of supercooled alloy with amorphous structure, can be applied for imprinting deformation because of their smooth surfaces and viscous flow behavior in the supercooled liquid region.

In FIG. 2, the cross-section of each pattern 204 is rectangular. However, from top view, each of the patterns 204 is, for example, a rectangular shape, a triangular shape, a circular shape, a rhombic shape, an elliptical shape, a hexagonal shape, or an octagonal shape. In other embodiments, the cross-section of each pattern 204 may be semi-circular, wave-shaped, or trapezoidal, and it is not limited to rectangular. Each of the patterns 204 preferably has a size S with nanoscale, e.g. 10-100 nm; alternatively, the size S may be microscale, e.g. 0.1-10 μm. Moreover, since the patterns 204 are generally formed by imprinting, it is possible to keep a little metallic glass (not shown) among those patterns 204.

In order to verify the effect of this invention, please refer to following describes examples. However, the scope of this invention is not limited to the following examples.

Analysis Techniques

1. X-ray Diffraction (XRD) for crystal structure.
2. Transmission Electron Microscope (TEM) for crystal structure.
3. Spectroscopic Ellipsometer (J.A. Woolam Co, M2000 ELLIPSOMTER) for dielectric function.
4. Scanning Electron Microscope (SEM) for microscope structure.
5. Raman Spectrometer for Raman spectrum.

Preparation

A thin film metallic glass with thickness of 50 nm was prepared by the co-sputtering process on BK7 (n=1.5168) glass substrate. The co-sputtering process is performed by using a gold (Au) target and a CuSi target, and the temperature of substrates keeping under 15° C. The resulting thin film metallic glass are $Au_{35}Cu_{28}Si_{37}$, $Au_{49}Cu_{22}Si_{29}$, $Au_{61}Cu_{19}Si_{20}$, and $Au_{65}Cu_{17}Si_{17}$ represented by R30, R40, R50 and R55, respectively.

Figure 3A:
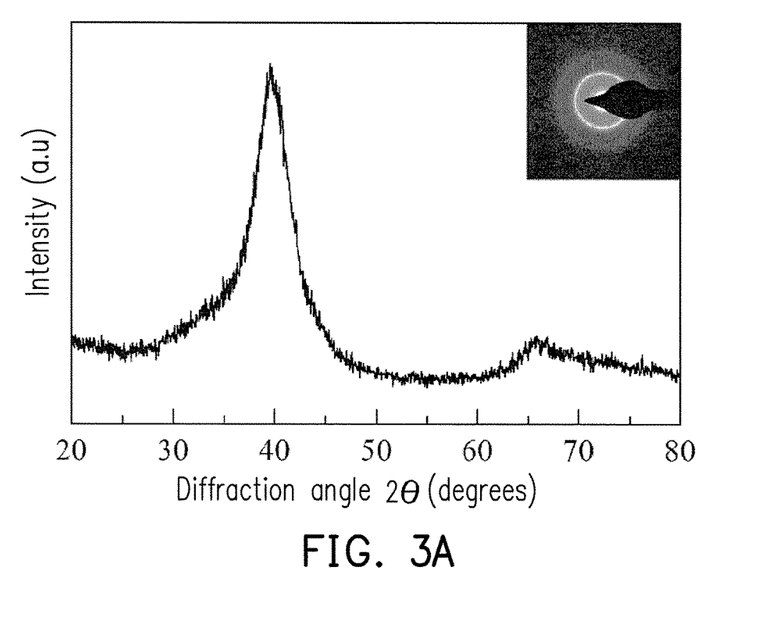
FIG. 3A is an X-ray Diffraction (XRD) spectrum of Preparation (R55).

The XRD spectrum of R55 is shown in FIG. 3A, and the diffraction pattern of TEM is inset in the upper-right of FIG. 3A. No obvious crystalline peaks were observed in the spectrum and the broad peak at ~40° supported the formation of amorphous structure of the film.

The amorphous structure was further confirmed by TEM in the upper-right of FIG. 3A. The diffused halo rings in the diffraction pattern in the inset provided the strong evidence for the formation of fully amorphous structure. In the absence of grain boundaries in the amorphous structure, grain boundary scattering of the light does not occur.

Figure 3B:
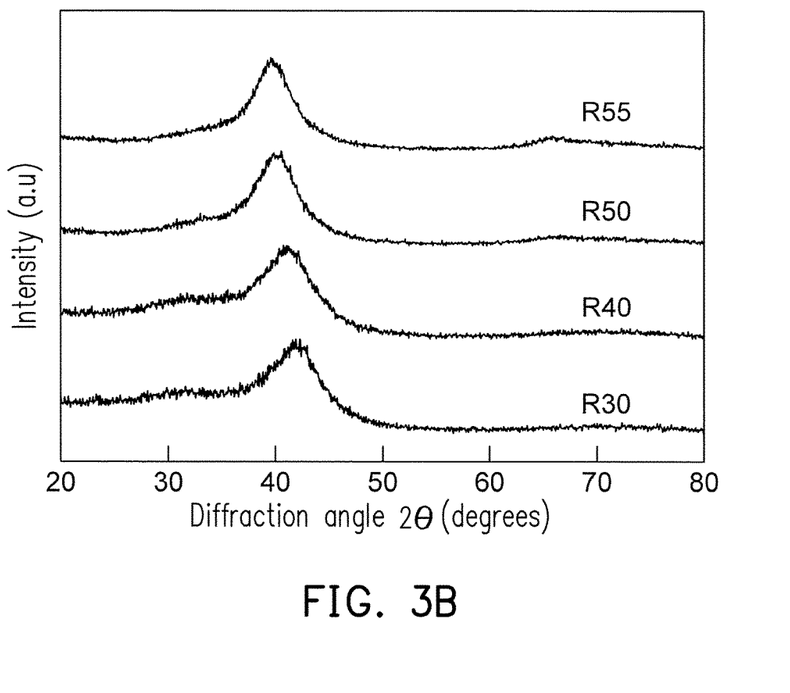
FIG. 3B is an XRD spectrums of R30, R40, R50, and R55.

The XRD spectrum of R30, R40, R50, and R55 is shown in FIG. 3B. No obvious crystalline peaks were observed in the spectrum and the broad peak at ~40° supported the formation of amorphous structure of the film.

Comparative Preparation 1

A gold (Au) thin film was formed on BK7 (n=1.5168) glass substrate.

Comparative Preparation 2

A silver (Ag) thin film was formed on BK7 (n=1.5168) glass substrate.

Detection for Dielectric Function

For plasmonic sensors, the desired resonance wavelength supporting the strong surface plasmon is a critical issue. The ability of a metal to produce the surface plasmon is dependent on its dielectric properties, which represent the physical interaction between its orbital electrons and the light and has a real part of dielectric constant ($\varepsilon_r$) and an imaginary part of dielectric constant ($\varepsilon_i$) varying with excitation wavelength ($\lambda$).

Figure 4:
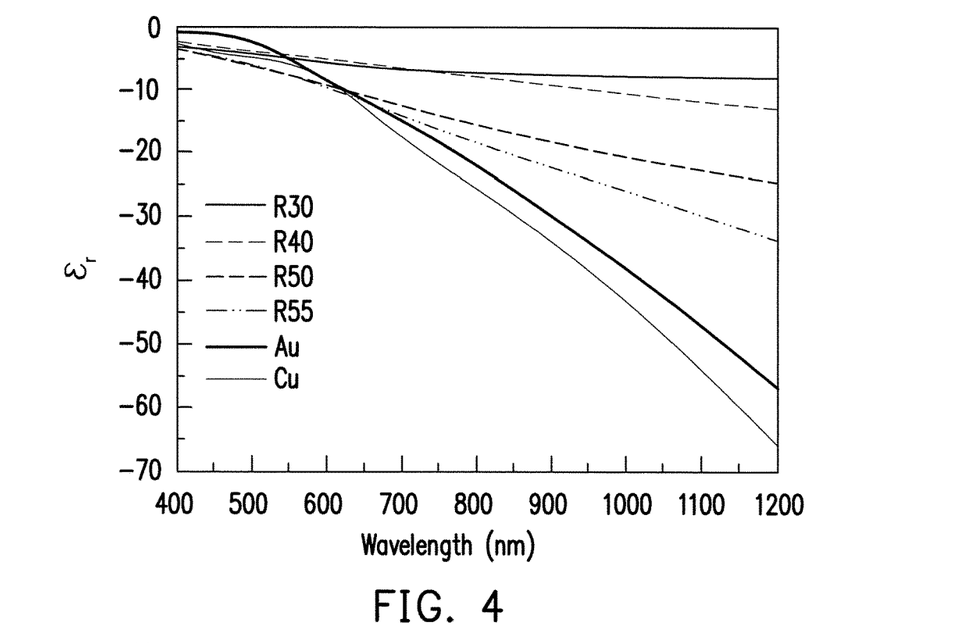
FIG. 4 shows curves illustrating the real part of dielectric constant ($\varepsilon_r$) of Preparation, Comparative Preparation 1 and Comparative Preparation 2, respectively.

To obtain the dielectric function of the Preparation, the spectroscopic ellipsometer is utilized to measure the real part ($\varepsilon_r$) and the imaginary part ($\varepsilon_i$). FIG. 4 shows curves illustrating the real part of dielectric constant ($\varepsilon_r$) of Preparation, Comparative Preparation 1 and Comparative Preparation 2, respectively. In general, the real part ($\varepsilon_r$) is regarded as a dielectric constant of a material.

In FIG. 4, Comparative Preparation 1 (Au) and Comparative Preparation 2 (Ag) show negative $\varepsilon_r$ and small $\varepsilon_i$ for the small loss during the light interaction, where the dielectric property of Ag and Au are the most popular and conventional metals to produce sufficiently strong LSPR and PSPR for plasmonic applications.

By contrast, the Preparation (R30, R40, R50, and R55) also has the excellent dielectric function as shown in FIG. 4. It can be seen that the real part of dielectric function ($\varepsilon_r$) is negative and smaller than those of Comparative Preparation 1 (Au) and Comparative Preparation 2 (Ag) for the wavelength smaller than 800 nm.

Figure 5:
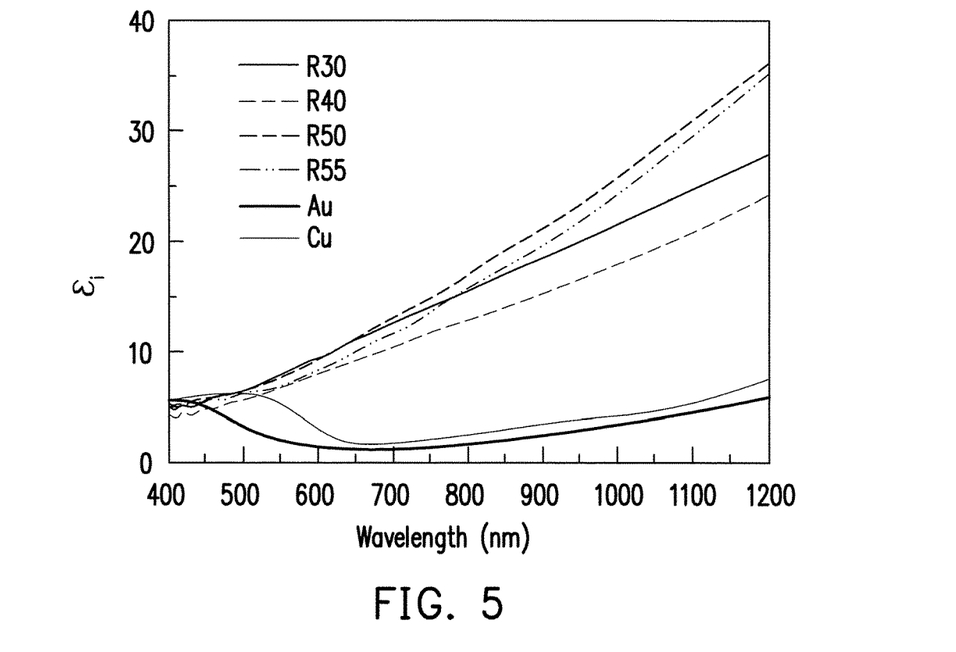
FIG. 5 shows curves illustrating the imaginary part of dielectric constant ($\varepsilon_i$) of Preparation, Comparative Preparation 1 and Comparative Preparation 2, respectively.

FIG. 5 shows curves illustrating the imaginary part of dielectric constant ($\varepsilon_i$) of Preparation, Comparative Preparation 1 and Comparative Preparation 2, respectively. In FIG. 5, the imaginary part ($\varepsilon_i$) of dielectric function is larger than those of Comparative Preparation 1 and Comparative Preparation 2.

Example 1

Figure 6A:
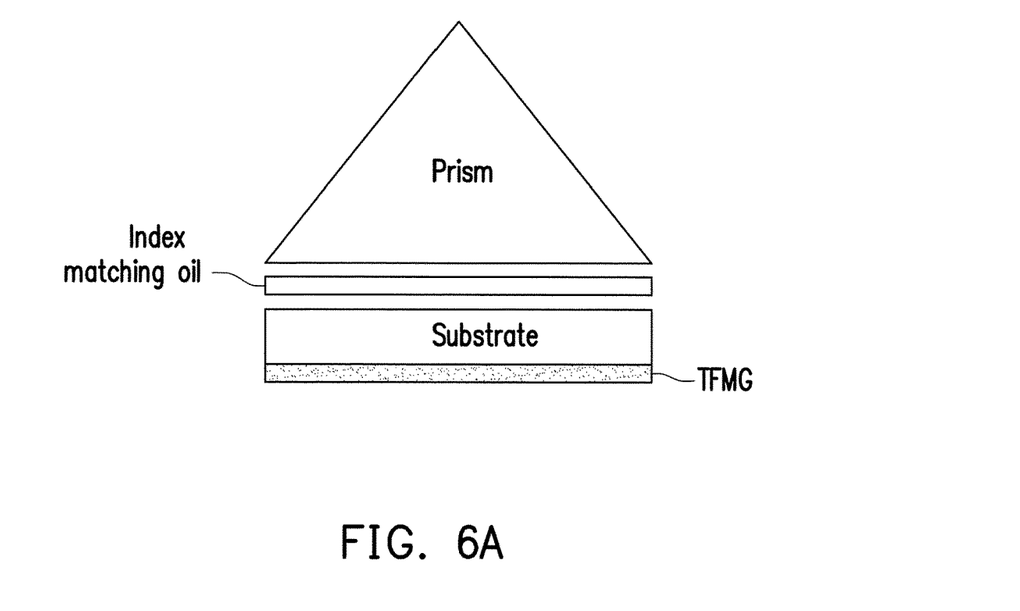
FIG. 6A is a cross-sectional schematic diagram of an instrument set-up for PSPR of Example 1.

The thin film metallic glass (TFMG) and the BK7 glass substrate of the Preparation (R55) were attached to a BK7 prism with index matching oil (n=1.5150±0.0002) for PSPR of Example 1 as shown in FIG. 6A. The BK7 prism is used as a spectroscope; however, the invention is not limited thereto. The prism may be replaced by semicircular in other embodiments.

Figure 6B:
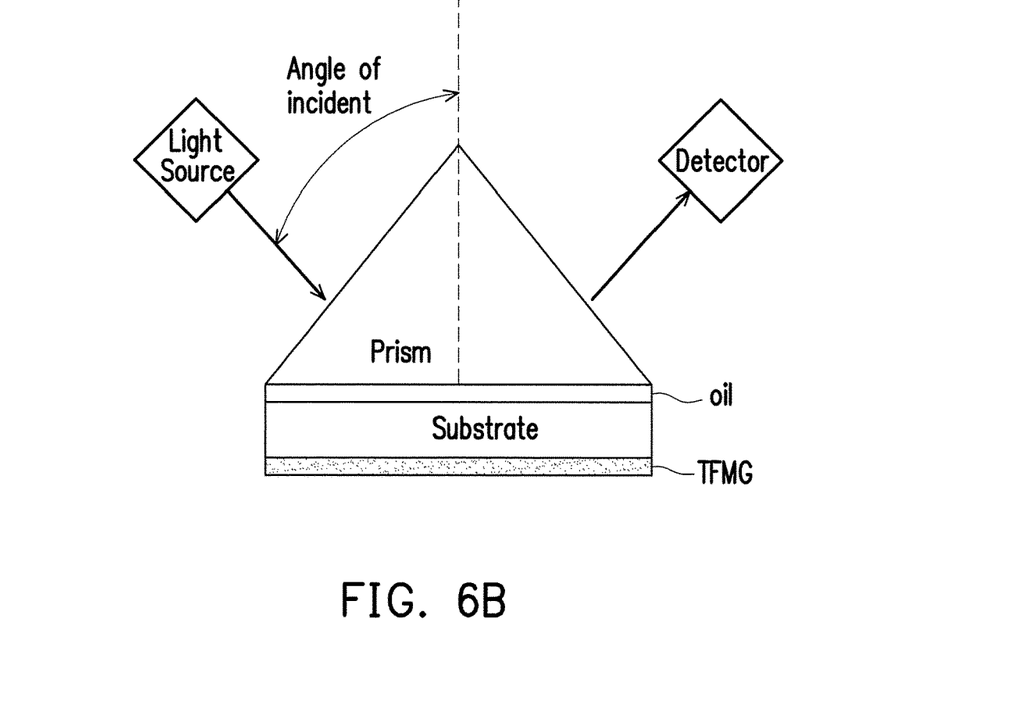
FIG. 6B is a cross-sectional schematic diagram of the instrument of FIG. 6A during PSPR measurement.

FIG. 6B is a cross-sectional schematic diagram of the instrument of FIG. 6A during PSPR measurement. In detail, de-ionized water ($H_2O$) and ethyl alcohol ($C_2H_5OH$) with refractive indexes of 1.333 and 1.361, respectively, were used as analytes in a container for the PSPR measurement. A polarized incident light with wavelength from 370 to 1690 nm was illuminated through the prism onto the TFMG. The prism, the TFMG, and the container were fixed on the stage. The reflectance of Example 1 and Comparative Example 1 was measured by the spectroscopic ellipsometer with angle of incident from 45° to 85°, and the results were shown in FIG. 7.

Comparative Example 1

The gold (Au) film and the glass substrate of Comparative Preparation 1 were attached to a BK7 prism with the index matching oil, and then the PSPR measurement was performed as FIG. 6B. The result is also shown in FIG. 7.

Figure 7:
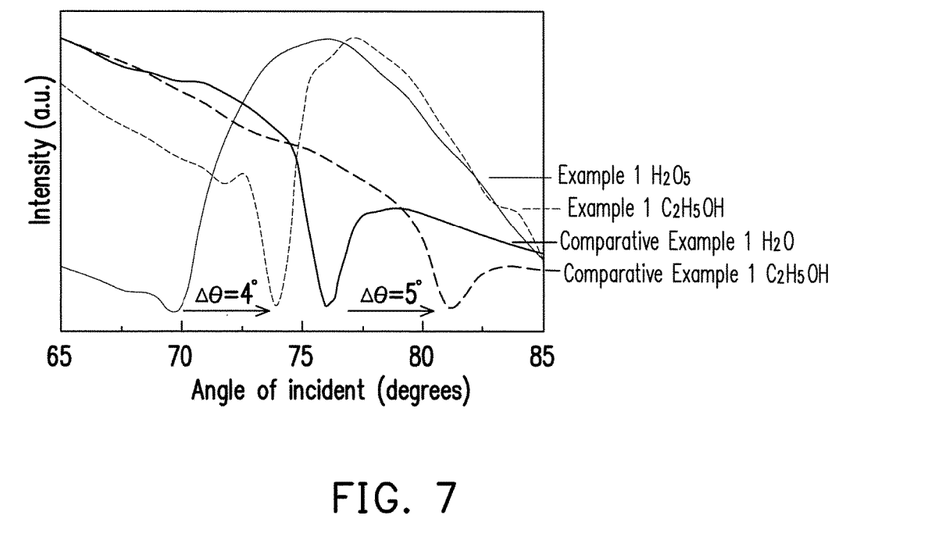
FIG. 7 shows a PSPR analysis for $H_2O$ and $C_2H_5OH$ according to Example 1 and Comparative Example 1.

In FIG. 7, the SPR angle, at which the reflectance in p-direction is minimal in the reflectance intensity versus incident angle curve, shifts with different analytes, as shown in FIG. 6B. The shift angle, $\Delta\theta_{SPR}$, of Comparative Example 1 (Au) and Example 1 (TFMG) for the incident wavelength of 850 nm were 5° and 4°, respectively, as the analyte was switched from de-ionized water to ethyl alcohol. Therefore, it is concluded that the TFMG is good plasmonic materials for PSPR sensors.

Example 2

Figure 8:
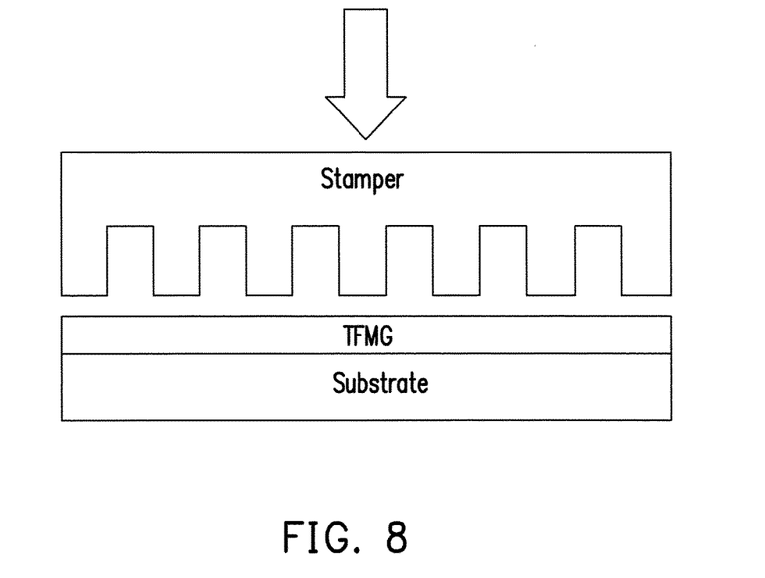
FIG. 8 is a cross-sectional schematic diagram of imprinting process for SCLR of Example 2.
Figure 9A:
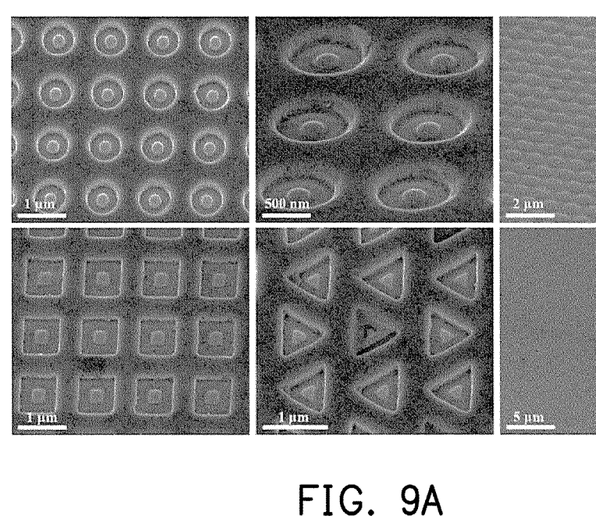
FIG. 9A shows six SEM images of the imprinted films consisting of patterns with different shapes and sizes, respectively.
Figure 9B:
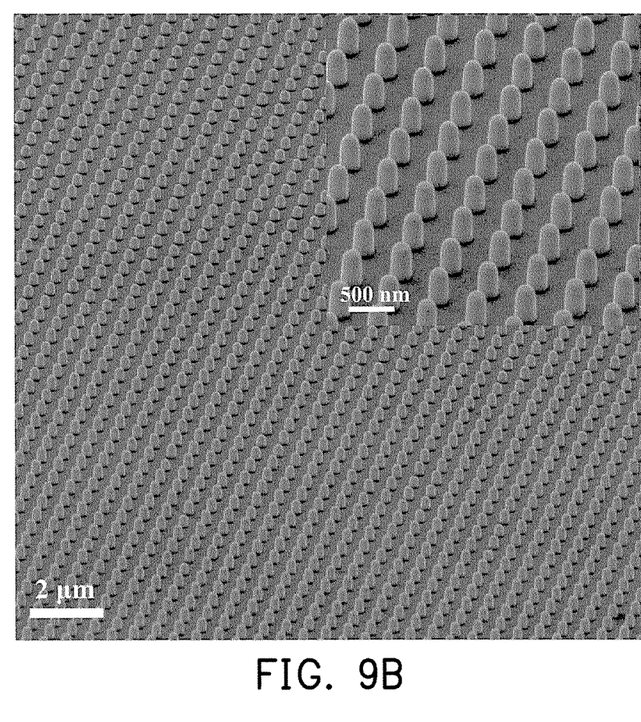
FIG. 9B shows a SEM image of the film consisting of patterns by capillary effect.

The patterns with nanoscale on the surface of the TFMG of Example 1 were fabricated by embossing the stamper onto the TFMG within SCLR as shown in FIG. 8. The size of each patterns is able to as large as stamper. Then, the stamper was retreated when the temperature decreased to below 0.8 $T_g$. According to this method, nano-structured patterns with different shapes and sizes could be fabricated, as shown in the SEM images of FIGS. 9A and 9B, respectively. Each of the patterns in FIG. 9A is intruded into the top surface of the imprinted film, while the patterns in FIG. 9B are extruded from the bottom surface of the imprinted film due to capillary effect.

Comparative Example 2

A gold film (~40 nm in thickness) was coated on the top of a nano-structured Si substrate. The nano-structured Si substrate has the same size as the patterns of Example 2.

Figure 10:
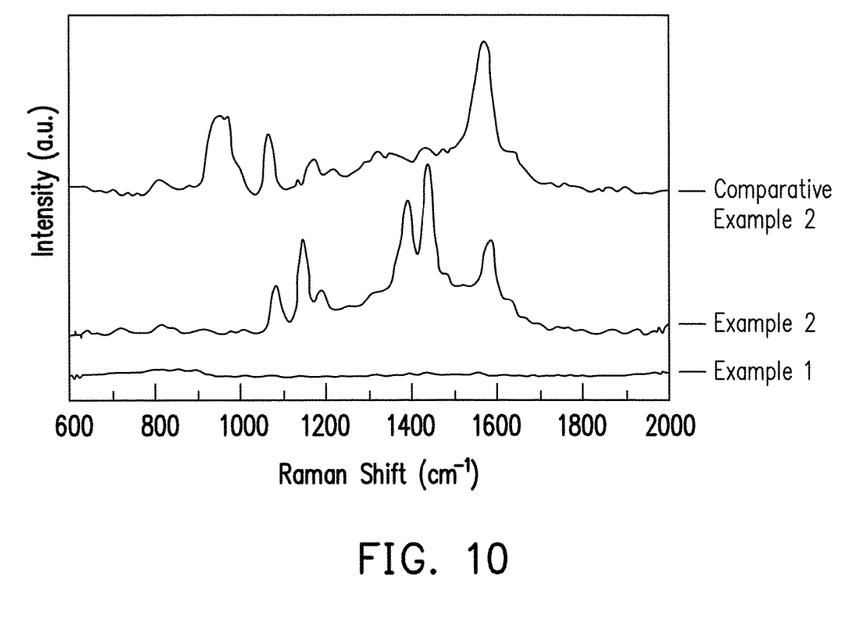
FIG. 10 shows curves illustrating Raman spectra of p-aminothiolphenol (p-ATP) according to Example 1, Example 2 and Comparative Example 2.

For Raman spectroscopy, the self-assembled molecule of p-aminothiolphenol (p-ATP) was selected as the analyte to ensure the monolayer adsorption of molecules on the surface of the nano-structure. The imprinted sample was soaked in the $10^{-3}$ M p-ATP dilute solution for 12 hours. The corresponding Raman spectrum is shown in FIG. 10.

Similar to Comparative Example 2 (Au patterns), Example 2 (imprinted TFMG) is able to reveal characteristic peaks of analyte effectively. On the other hand, there is no obvious peak in the spectrum for Example 1, and it provides a strong evidence that imprinted TFMG with nano-structured patterns has great Raman enhancement effects. Compared with Comparative Example 2, the vibrational characteristic peaks of the analyte for Example 2 were much more distinguishable, and the process for Example 2 is much more efficient and easier. The TFMG is amorphous, and grain boundary scattering does not occur. In addition, because Au is only coated on the top of the Si substrate in Comparative Example 2, the incomplete coverage of Si by Au on the side-surface would result in a strong vibrational signal of Si at ~900 $cm^{-1}$ (as shown in FIG. 10), which may overlap the signals of analyte and decrease the accuracy of sensing.

Based on the above, the invention provides a thin film metallic glass with negative dielectric constant, and thus it is suitable for plasmonic sensor applications, including propagating surface plasmon resonance (PSPR) sensors and localized surface plasmon resonances (LSPR) sensors. Accordingly, the plasmonic sensor according to the invention is useful in a wide variety of applications, including but not limited to energy absorption, biomedical sensing, light harvest collection, thermal management, chemical detection, and photocatalyst applications.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A plasmonic sensor, being a propagating surface plasmon resonance (PSPR) sensor, comprising:
   a substrate having a first surface and a second surface opposite to the first surface;
   a thin film metallic glass, formed on the first surface of the substrate, wherein a dielectric constant ($\varepsilon_r$) of the thin film metallic glass is negative, and a material of the thin film metallic glass comprises $Au_{35}Cu_{28}Si_{37}$, $Au_{49}Cu_{22}Si_{29}$, $Au_{61}Cu_{19}Si_{20}$, or $Au_{65}Cu_{17}Si_{17}$; and
   a spectroscope, attached to the second surface of the substrate.

2. The plasmonic sensor according to claim 1, wherein a thickness of the thin film metallic glass is 10 nm to 10,000 nm.

3. The plasmonic sensor according to claim 1, wherein the substrate comprises glass substrate, silicon substrate, sapphire substrate, metal substrate, or flexible substrate.

4. A plasmonic sensor, being a localized surface plasmon resonances (LSPR) sensor, consists of a substrate and a thin film metallic glass formed on the substrate, wherein
a dielectric constant ($\varepsilon_r$) of the thin film metallic glass is negative,
a material of the thin film metallic glass comprises $Au_{35}Cu_{28}Si_{37}$, $Au_{49}Cu_{22}Si_{29}$, $Au_{61}Cu_{19}Si_{20}$, or $Au_{65}Cu_{17}Si_{17}$, and
the thin film metallic glass is an imprinted film consisting of a plurality of patterns, and the patterns are arranged periodically or randomly, wherein each of the patterns is extruded from a bottom surface of the thin film metallic glass, and the bottom surface is in direct contact with the substrate.

5. The plasmonic sensor according to claim 4, wherein a thickness of the thin film metallic glass is 10 nm to 10,000 nm.

6. The plasmonic sensor according to claim 4, wherein the substrate comprises glass substrate, silicon substrate, sapphire substrate, metal substrate, or flexible substrate.

7. The plasmonic sensor according to claim 4, wherein each of the patterns is extruded from a bottom surface of the imprinted film.

8. The plasmonic sensor according to claim 4, wherein each of the patterns is intruded into a top surface of the imprinted film.

9. The plasmonic sensor according to claim 4, wherein each of the patterns has a nano-scale size or a micro-scale size.

* * * * *